United States Patent [19]

Labino

[11] 4,259,860
[45] Apr. 7, 1981

[54] INSTRUMENT FOR MEASURING THE SOFTENING TEMPERATURE OF GLASS

[76] Inventor: Dominick Labino, P.O. Box 430, Grand Rapids, Ohio 43522

[21] Appl. No.: 30,002

[22] Filed: Apr. 16, 1979

[51] Int. Cl.³ ............................................. G01N 25/04
[52] U.S. Cl. ................................................... 73/17 R
[58] Field of Search ................................... 73/17 R, 83

[56] References Cited

U.S. PATENT DOCUMENTS

| | | | |
|---|---|---|---|
| 3,187,556 | 6/1965 | Ehlers | 73/17 |
| 3,289,460 | 12/1966 | Anderson | 73/17 |
| 3,580,047 | 5/1971 | Simpson | 73/17 |
| 3,630,073 | 12/1971 | Michel | 73/17 |
| 3,646,802 | 3/1972 | Nolting et al. | 73/17 |
| 4,116,048 | 9/1978 | Appleford | 73/17 |

*Primary Examiner*—Herbert Goldstein
*Attorney, Agent, or Firm*—Oliver E. Todd, Jr.

[57] ABSTRACT

Apparatus and a method are disclosed for measuring the softening temperature of a specimen of a thermoplastic material such as glass. Pressure is applied through a rod to the specimen as the specimen is heated to at least its softening temperature. When the rod penetrates a predetermined distance into the softened specimen, the temperature of the specimen is measured.

5 Claims, 3 Drawing Figures

INSTRUMENT FOR MEASURING THE SOFTENING TEMPERATURE OF GLASS

BACKGROUND OF THE INVENTION

This invention relates to measuring and testing and more particularly to an improved instrument for quickly and accurately measuring the softening temperature of glass and similar products.

In working with glass, it is often desirable to know the softening temperature of the glass. For example, a number of different colored glasses are commonly used in decorative or art glass, such as paperweights. If the different glass compositions used in a product have substantially different softening temperatures, it may be difficult or impossible to combine these compositions. In forming paperweights, for example, bits of glass having different colors may be adhered to the surface of a heated gob of clear glass. The gob of glass with the attached bits then is reheated until the bits of glass are sufficiently plastic to permit working into a desired design. After the design is formed, the paperweight is finished by adding an outer layer of clear glass, in a conventional manner. If the bits of colored glass should have an appreciably higher softening temperature than the gob of clear glass, the colored glass cannot be worked into a desired pattern without overheating the clear glass. In the manufacture of other products from glass, it also may be desirable or necessary to know the softening temperature of the glass. This is particularly true in research where new glass compositions are developed.

According to the prior art, it has been very difficult and time consuming for measuring the softening temperature of thermoplastic materials such as glass. The normal prior art method for measuring the softening temperature of a glass involves suspending the upper end of a uniform fiber formed from a specimen of the glass within a furnace. The fiber extends below the furnace into a chamber having a transparent window. A technician observes the lower end of the fiber through the window and the temperature within the furnace as the temperature is gradually increased. When the upper end of the fiber is heated to its softening temperature, the fiber will begin to elongate. When the fiber elongates at a predetermined rate, the technician records the temperature within the oven. A test of this type may take several hours and requires the presence of a technician to observe the fiber as it is heated to its softening temperature. As a consequence, the test is expensive to run. In addition, the specimens must be uniform both in diameter and in roundness over its entire length and must have a diameter falling within narrow range. Otherwise, the indicated softening temperature will be inaccurate.

SUMMARY OF THE INVENTION

According to the present invention, an improved instrument and method are provided for accurately and relatively quickly measuring the softening temperature of glass and similar thermoplastic materials. The presence of a technician is required only to initiate a test cycle. Once a test cycle is initiated, it automatically runs to completion and the technician may perform other duties.

According to the present invention, a specimen of glass to be tested is mounted in a specimen holder which is positioned in a furnace or oven. The specimen is positioned between a fixed anvil and a movable rod which exerts a constant predetermined pressure on the specimen. The rod has an end exterior to the oven which operates a switch when the rod penetrates a predetermined distance into the specimen. A thermocouple is positioned in contact with the specimen for measuring its temperature during the test cycle. After the specimen is mounted in the holder and positioned in the oven, an electric heating element is activated to progressively increase the temperature of the furnace. Preferably, the current to the heating element is increased over a period of time to progressively increase the rate at which the furnace is heated. This gradual increase in temperature permits the specimen to heat more uniformly throughout, as distinguished from placing the specimen in a preheated or a rapidly heated furnace which will more rapidly heat the surface of the specimen than its interior. When the specimen is heated to its softening temperature, the pressure exerted on the rod causes the rod to penetrate into the specimen. When the rod penetrates the predetermined distance into the softened specimen, the switch is released to cause the temperature of the specimen, as measured by the thermocouple, to be recorded and to interrupt power to the heating element. If desired, an alarm may be activated at the same time to notify the technician operating the instrument that the test cycle has been completed.

Accordingly, it is a preferred object of the invention to provide an improved instrument and method for measuring the softening temperature of glass and similar thermoplastic materials.

Another object of the invention is to provide an instrument and method for quickly and accurately measuring the softening temperature of glass and similar thermoplastic materials which does not require the presence of a technician during the entire testing cycle.

Other objects and advantages of the invention will become apparent from the following detailed description, with reference being made to the accompanying drawings.

DESCRIPTION OF THE PREFERRED EMBODIMENTS

Figure 1:
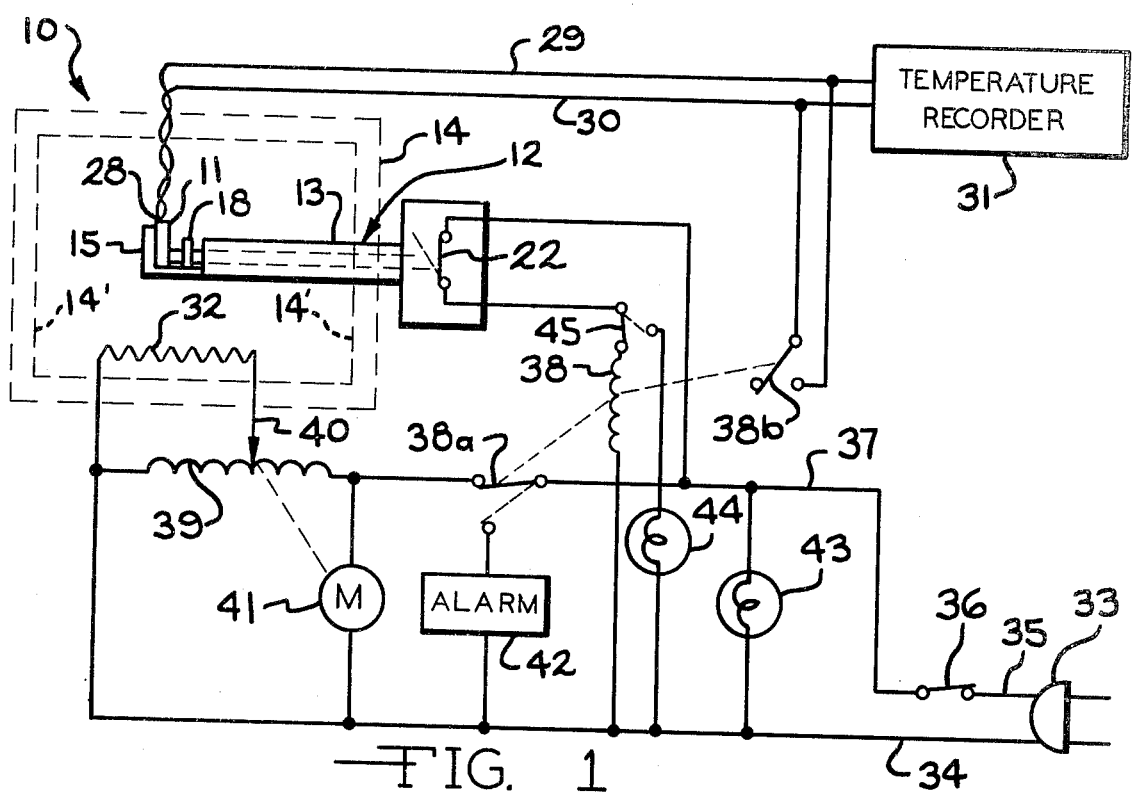
FIG. 1 is a schematic circuit diagram of an instrument for measuring the softening temperature of glass constructed in accordance with the present invention.

Turning now to the drawings and particularly to FIG. 1, an instrument 10 is shown constructed in accordance with the present invention for measuring the softening temperature of a specimen 11 of glass or of similar thermoplastic materials. Preferably, the specimen 11 is flat and has a thickness on the order of approximately 0.08 to 0.160 inch. Thicker specimens may be used. However, with thicker specimens it is necessary to prolong the test cycle so that the specimen is gradually heated throughout as distinguished from heating the surface more rapidly than the interior of the specimen.

Figure 2:
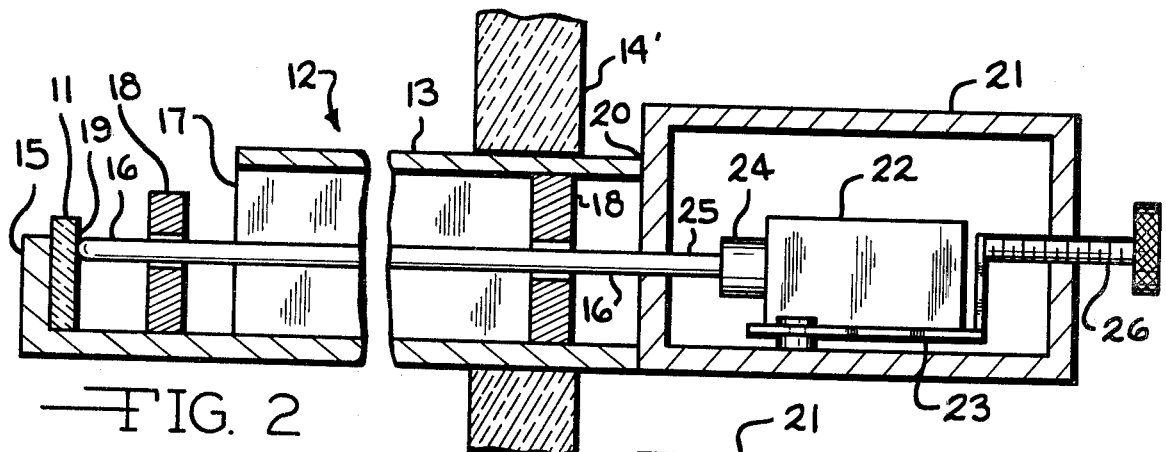
FIG. 2 is a side elevational cross sectional view of a specimen holder for use in the instrument of the present invention.
Figure 3:
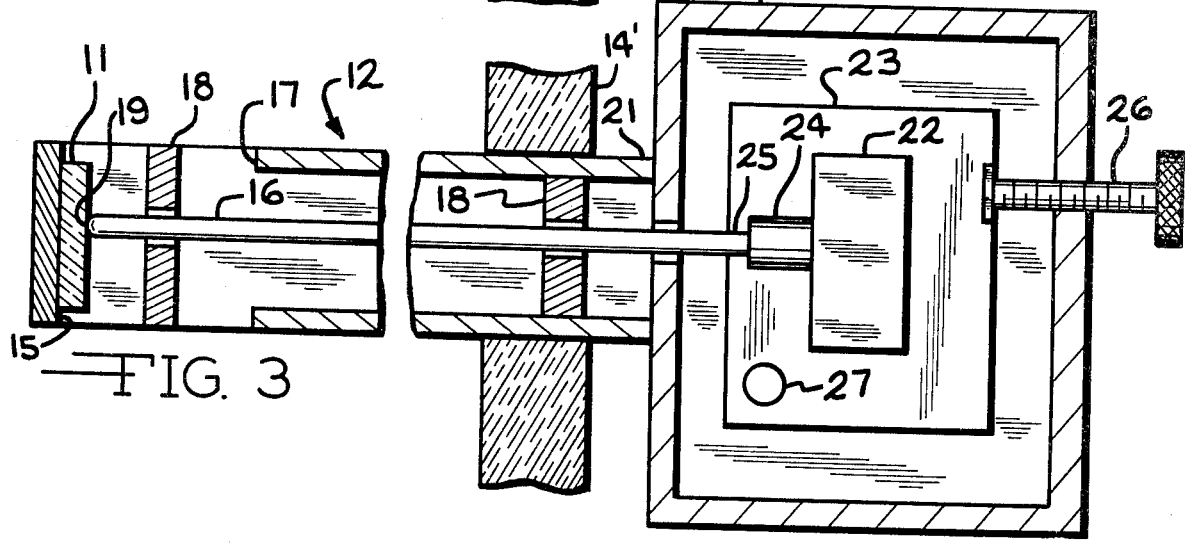
FIG. 3 is a top plan cross sectional view of the specimen holder of FIG. 2.

The specimen 11 is mounted in a specimen holder 12 which is shown in detail in FIGS. 1, 2 and 3. The specimen holder 12 includes a tubular section 13 which extends from outside a furnace 14, through a wall 14' of the furnace 14 to a location within the furnace 14. The tube 13 slides through an opening in the wall 14' of the furnace 14 so that the specimen holder 12 may be removed from the furnace 14 for replacing the specimen 11. The specimen 11 is positioned between an anvil 15 and a rod 16 located at an end 17 of the tube 13. Preferably, both the anvil 15 and the specimen 11 are flat and in contact with each other. The rod 16, which passes coaxially through the tube 13, is guided by two supports 18. The supports 18 restrict the rod 16 to move in an axial direction perpendicular to the anvil 15 and the specimen 11. A force is exerted on the rod 16 so that an end 19 of the rod 16 presses against the specimen 11. Although the rod end 19 may have various shapes, it has been found that forming a spherical surface to the rod end 19 produces highly uniform measurements of the softening temperatures of glass specimens 11.

The tube 13 also has an end 20 which is located exterior from the furnace 14. A housing 21 is attached to the tube end 20. A switch 22 is mounted on a support 23 within the housing 21. The switch 22 has an actuator 24 which contacts an end 25 of the rod 16. An adjustment screw 26 which threadably engages the housing 21 rotates the switch support 23 about a bearing 27. As the switch support 23 is rotated or pivoted on the bearing 27, the switch actuator 24 and the rod 16 are moved toward or away from the specimen 11 and the anvil 15. Of course, it will be appreciated that the switch support 23 may take on other forms and may be mounted in the housing 21 for linear adjustment towards and away from the specimen 11 and anvil 15 rather than pivotal movement. The primary consideration is that the relative position of the switch actuator 24 and the rod 16 must be adjustable with respect to the anvil 15.

Returning again to FIG. 1, the specimen holder 12 is shown holding the specimen 11 within the furnace 14. After the specimen holder 12 is positioned as shown, a thermocouple 28 is moved into contact with the surface of the specimen 11 for measuring its temperature. The thermocouple 28 is connected through a pair of wires 29 and 30 to a temperature recorder 31. The temperature recorder 31 monitors the temperature of the specimen 11 as it is heated within the furnace 14 during a test cycle.

During the test cycle, power is applied to an electric heating element 32 which is located for heating the furnace 14. The instrument 10 may be operated from a conventional commercial power source, such as a 110 to 120 volt A.C. power source in the United States. The instrument 10 includes a plug 33 for connection to the power source. The plug 33 is connected to a conductor or wire 34 which connects to one side of the heating element 32 and through a conductor 35 to a power switch 36. When closed, the switch 36 connects the conductor 35 to a terminal 37. When closed, the normally open contacts of a relay actuated switch 38a connect a variable voltage transformer 39 between the terminal 37 and the line 34. The heating element 32 is connected between an adjustable tap 40 on the transformer 39 and the conductor 34. A motor 41 is connected in parallel with the transformer 39 to gradually change the position of the tap 40 to increase the current through the heating element 32 as the test cycle for the specimen 11 progresses.

A connection also is made from the terminal 37 through the switch 22 and a relay winding 38 to the conductor 34. The winding 38 actuates two single pole-double throw switches 38a and 38b. At the beginning of a test cycle, the switch 22 is closed so as to energize the relay coil 38, to in turn actuate the two relay switches 38a and 38b. When the relay switch 38a is actuated, the terminal 37 is connected to the motor 41 and to the transformer 39 for applying power to the heater element 32. The motor 41 in combination with the transformer 39 causes an increasing current to be applied to the heating element 32 for gradually increasing the temperature at which the specimen 11 is heated within the oven 14. When the specimen 11 is heated to its softening point, the rod 16 will penetrate the specimen 11 sufficiently to allow the switch 22 to open. This in turn de-energizes the relay coil to release the two relay switches 38a and 38b. When the switch 38a is released, power to the motor 41, the transformer 39 and the heating element 32 is interrupted. At the same time, power may be applied from the terminal 37 through the normally closed contacts of the relay switch 38a to an alarm 42 for notifying a technician that a testing cycle has been completed. When the other set of relay contacts 38b are released by de-energizing the relay coil 38, the contacts 38b short together the wires 29 and 30 which connect the thermocouple 28 to the temperature recorder 31. As a consequence, the temperature recorder 31 will cease recording a temperature. If the temperature recorder 31 is a chart recorder, the last temperature indicated on the chart before the pen returns to 0 will be the softening temperature of the specimen 11. Or, in a modified embodiment of the apparatus 10, the temperature recorder 31 may be in the form of a digital recorder having an internal memory. When the specimen 11 reaches its softening temperature and the switch 22 is opened, the relay contacts 38b are connected to the recorder 31 to cause the temperature measured by the thermocouple 28 to be stored within the memory and displayed on a digital readout. Of course, other well known methods for indicating the temperature of the specimen 11 at the time the switch 22 is released will be readily apparent to those skilled in the art.

If desired, a pilot light 43 can be connected between the terminal 37 and the conductor 34 for indicating when the power switch 36 is closed and power is applied to the instrument 10. Also, a timer (not shown) can be connected in parallel with the motor 41. Such a timer will indicate the elasped time from the beginning of a test cycle to the completion of the test cycle.

Several tests were run on specimens of the same glass composition. The specimens which were samples of commercial bottle glass, had a thickness of approximately 1/10 inch and were placed in a specimen holder 12 having a 1/10 inch diameter rod 16 with a spherical end 19 contacting the specimen. The specimen holder 12 was provided with a snap action switch 22 which exerted a force of approximately 75 grams through a leaf actuator 24 to the rod end 25. The snap action switch 22 had a pretravel of about 0.025 inch so that the switch 22 was released when the rod 16 moved only 0.025 inch. A specimen of the glass was placed in the specimen holder 12 between the anvil 15 and the rod 16. The adjustment screw 26 was then turned to move the switch 22 until the switch 22 just closed. The screw 26 was further rotated by a small increment to slightly increase the travel of the rod 16 required to release the switch 22. The end of the specimen holder 12 containing the specimen 11 then was inserted through the wall 14' of the oven or furnace 14 and the thermocouple 28 was positioned in contact with the surface of the specimen 11. The electric heating element 32 within the oven 14 was then energized to initiate a test cycle. The rate at which the heating element 32 heated the oven 14 was varied through tests of three specimens and the following softening temperatures and cycle times were noted:

| SPECIMEN NO. | CYCLE TIME | INDICATED SOFTENING TEMPERATURE |
|---|---|---|
| 1 | 21.3 minutes | 1377° F. |
| 2 | 20.9 minutes | 1372° F. |
| 3 | 21.1 minutes | 1370° F. |

In each case, the indicated temperatures were very close to the average reading of 1373° F.

In a second series of three tests on specimens of a different glass, the cycle time was varied and the following results were noted:

| SPECIMEN NO. | CYCLE TIME | INDICATED SOFTENING TEMPERATURE |
|---|---|---|
| 1 | 22 minutes | 1350° F. |
| 2 | 25 minutes | 1345° F. |
| 3 | 32 minutes | 1335° F. |

It will be noted that decreasing the cycle time will increase the indicated softening temperature. This is because the surface of the specimen will heat appreciably faster than the center of the specimen when the furnace temperature is increased to decrease the cycle time. By the time the center of the specimen has heated to a point sufficient to allow the rod 16 to penetrate, the indicated surface temperature will be above the softening temperature for the specimen.

If desired, an indicator lamp 44 may be connected in parallel with the relay coil 38. The lamp indicates when the switch 22 is open or closed during adjustment of the screw 26 when a new specimen is placed in the workholder 12. A manual single pole-double throw switch 45 may be added to selectively connect either the relay coil 38 or the test lamp in circuit with the switch 22. In this case, when the test lamp 44 is connected for adjustment of the screw 26, only the indicator lamp will be energized when the switch 22 is closed rather than both the indicator lamp and the parallel motor 41 and heating element 32.

It should be noted that the softening temperature of materials such as glass are imprecise and generally are defined by standard tests. In recent times, the softening point for glass has been defined as a specific point on a viscosity curve, i.e., a viscosity of $10^{7.65}$ poises. The softening temperature of a glass specimen will be the temperature at which the specimen has this viscosity. The softening temperature of glass is imprecise because glass is an amorphous material which becomes less and less viscous as it is heated without passing through a distinct transformation. As a consequence, the softening temperature indicated by the instrument 10 will be affected by the diameter of the rod 16 and by the pressure exerted by the rod 16 on the specimen 11. If the rod diameter is decreased or the pressure on the rod is increased, the rod 16 will penetrate the specimen 11 at a somewhat lower temperature, or when the specimen has a higher viscosity. Or a higher softening temperature will be indicated when the diameter of the rod 16 is increased or the pressure on the rod 16 is decreased. By adjusting the rod pressure and selecting the proper rod diameter, the instrument 10 can be calibrated to indicate the same softening temperatures indicated by prior art tests.

It will be appreciated that various changes and modifications may be made in the above described preferred embodiment of an instrument 10 for measuring the softening temperature of glass and similar materials without departing from the spirit and the scope of the following claims. For example, the switch 22 which has been described as a normally opened switch may be replaced with a normally closed switch merely by changing the connections to the terminals of the relay switches 38a and 38b. Other similar changes also will be apparent to those skilled in this art.

What I claim is:

1. Apparatus for measuring the softening temperature of a specimen of glass comprising a furnace, means for heating said furnace to at least the softening temperature of the specimen, means for holding the specimen in said furnace including an anvil, a rod having first and second ends and means for mounting said rod for linear movement in a direction substantially perpendicular to said anvil, the specimen fitting between said first rod end and said anvil, means for biasing said rod towards said anvil with a predetermined force whereby said first rod end exerts the predetermined force on the specimen, switch means for detecting when said rod end has penetrated a predetermined distance into the specimen upon such specimen reaching its softening temperature comprising a snap action switch having an actuator and means positioning said actuator against said second rod end with said switch actuated, said switch releasing when said rod penetrates said predetermined distance into the specimen, and means responsive to said switch means for measuring the softening temperature of the specimen.

2. Apparatus for measuring the softening temperature of a specimen of glass, as set forth in claim 1, wherein said softening temperature measuring means comprises thermocouple means for measuring the temperature of the specimen as the specimen is heated in said furnace, and means responsive to the releasing of said switch when said rod penetrates the specimen for recording the specimen temperature measured by said thermocouple means.

3. Apparatus for measuring the softening temperature of a specimen of glass, as set forth in claim 2, and further including an alarm, and means responsive to the releasing of said switch when said rod penetrates the specimen for energizing said alarm.

4. Apparatus for measuring the softening temperature of a specimen of glass, as set forth in claim 2, and further including means responsive to the releasing of said switch when said rod penetrates the specimen for stopping said heating means from further heating said furnace.

5. Apparatus for measuring the softening temperature of a specimen of glass, as set forth in claims 1 or 2, and wherein said biasing means comprises said switch actuator.

* * * * *